United States Patent [19]

Shillington et al.

[11] Patent Number: 5,230,496

[45] Date of Patent: Jul. 27, 1993

[54] POLE MOUNTING CLAMP

[75] Inventors: Richard A. Shillington, Leucadia; Gilbert Packer, Carlsbad, both of Calif.

[73] Assignee: Med-Safe Systems, Inc., Carlsbad, Calif.

[21] Appl. No.: 740,815

[22] Filed: Aug. 6, 1991

[51] Int. Cl.$^5$ .............................................. A47G 1/10
[52] U.S. Cl. .................... 248/316.5; 24/487; 24/543; 248/74.1; 248/218.4
[58] Field of Search ............ 245/316.5, 231, 229, 245/74.1, 74.2, 218.4, 230, 316.1; 24/487, 543, 557

[56] References Cited

U.S. PATENT DOCUMENTS

| | | | |
|---|---|---|---|
| 3,913,187 | 10/1975 | Okuda | 24/255 |
| 4,128,918 | 12/1978 | Wenk | 24/543 X |
| 4,214,351 | 7/1980 | Wenk | 24/543 X |
| 4,291,855 | 9/1981 | Schenkel et al. | 248/74.1 |
| 4,386,752 | 6/1983 | Paulak et al. | 248/73 |
| 4,566,660 | 1/1986 | Anscher et al. | 248/74.2 |
| 4,635,886 | 1/1987 | Santucci et al. | 248/73 |
| 4,762,296 | 8/1988 | Kraus | 248/74.2 |
| 4,835,824 | 6/1989 | Durham et al. | 24/339 |
| 4,917,340 | 4/1990 | Junemann et al. | 24/543 X |
| 4,955,574 | 8/1990 | Freier | 248/316.5 |

FOREIGN PATENT DOCUMENTS 2183287 6/1987 United Kingdom ............... 248/74.1

Primary Examiner—Ramon O. Ramirez
Attorney, Agent, or Firm—Baker, Maxham, Jester & Meador

[57] ABSTRACT

A mounting clamp for mounting a medical device on a vertical IV mounting pole comprises a base member for attachment to an article to be supported, a pair of arms having an inner end and an outer end and attached to the base at the inner end, a plurality of gripping fingers extending inward from the arms for gripping a support pole, and a latching finger at the outer end of each of the arms.

19 Claims, 1 Drawing Sheet

POLE MOUNTING CLAMP

BACKGROUND OF THE INVENTION

The present invention relates to mounting clamps and pertains particularly to an improved pole mounting clamp for mounting medical devices and the like to vertical support poles.

Intravenous therapy is widely and extensively used at bedside in hospitals and clinics. A major piece of equipment used in such therapy is the IV pole, which is a vertically extending cylindrical pole supported on a wheeled base to make it portable. The IV pole serves as a support stand for IV bags or reservoirs and associated or related equipment. Many other related medical articles, such as support structures for IV tubes, needles, needle caps and other items, are detachably secured to the pole by means of clamps.

The typical mounting clamp that is currently used has a hook like portion that extends around the pole, with an opposing hand screw that screws into tight engagement with the opposite side of the pole. These clamps have many drawbacks. Among these drawbacks are that they are bulky, cumbersome and difficult to attach and detach without the use of both hands. Another drawback is that they are expensive to manufacture.

One recently developed item for attachment to an IV pole is a needle cap or sheath holder, such as covered in U.S. Pat. No. 5,005,793, issued Apr. 9, 1991, to Richard A. Shillington, co-inventor herein. The needle cap holder is detachably attached to a pole by means of an elastic clip or clamp. The needle cap or sheath holder is a passive holder designed to reduce the incidence of needle pricking of the user's hands when re-capping needles. It is desirable to have these conveniently available where needles are used.

We have developed a mounting clamp that can be attached and detached to different size support poles and holds any number of different articles to the pole.

SUMMARY AND OBJECTS OF THE INVENTION

It is the primary object of the present invention to provide an improved clamp for mounting different articles to different size IV poles.

In accordance with a primary aspect of the present invention, a clamp member includes a base member, with arm means extending outward from the base for extending and latching around a supporting pole for holding a plurality of different articles in place on a vertical support pole.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
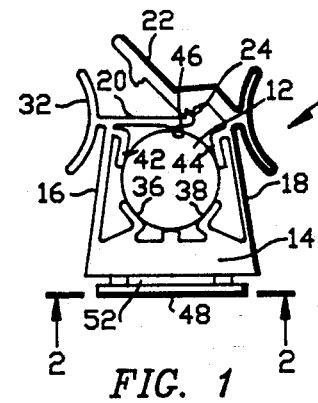
FIG. 1 is a top plan view illustrating a preferred embodiment of the invention attached to a typical support pole.

Referring to FIG. 1 of the drawings, an exemplary embodiment of a mounting clamp in accordance with the invention is illustrated and designated generally by the numeral 10. The mounting clamp was devised to quickly and easily attach and detach medical related articles, such as holders and the like, to vertically oriented support pole structure, such as IV support poles. The clamp structure, as will be explained, is designed to clamp securely to poles of different sizes. The illustrated mounting clamp is shown in FIG. 1 extending around and clamped to a vertically oriented cylindrical IV pole 12.

The clamp comprises a base or main body member 14 having a pair of outwardly and generally parallel extending arms 16 and 18 extending outward from each end thereof for partially encircling a mounting pole. Each of the respective outwardly extending arms 16 and 18 have, at their outer ends, inwardly directed inner and outer latching fingers 20 and 22.

In the illustrated embodiment, an inner latching finger 20 extends generally outward from arm 16 at about right angles to the 16 toward arm 18, arm and has a latching hook or pawl 24 at the outermost end thereof. An outer latching finger 22 extends outward at about forty-five degrees from the arm 18 toward arm 16, and includes a plurality of ratchet teeth in the illustrated embodiment positioned in two groups 26 and 28 extending along the inner surface of the arm to be engaged by the ratchet pawl 24. The outer latching finger 22 has a latch release tab 30 at the outer end thereof.

Each of the arms 16 and 18 are provided with finger squeeze tabs 32 and 34 at the outer ends thereof at the juncture of the latching fingers for squeezing the arms together around a support pole, and forcing the latching fingers 20 and 22 into latching engagement. These tabs may be engaged, for example, between a thumb and forefinger and squeezed inward around a support pole for one hand latching of the clamp to the pole.

The clamping unit or assembly is provided with clamping jaws or surfaces in the form of a plurality of yieldable fingers or tabs spaced around the inside the jaws for gripping engagement with the outer surface of a support pole. The fingers extend to an angle for engaging a cylindrical support pole tangentially. A first pair of gripping fingers 36 and 38 having a somewhat L configuration extend outward from the base member 14 and inward toward the inside of the jaws for engaging the outer cylindrical surface of the mounting pole 12. These fingers extend at an angle on the order of about forty-five degrees from the inner face of the base member 14, so that a side surface of the finger engages the pole. A gripping pad 40 may be provided between the fingers 36 and 38 for engaging the mounting pole.

A second pair of gripping fingers or tabs 42 and 44 having a generally L shape extend outward from the arms and inward toward the pole gripping area and generally parallel to the respective arms 16 and 18 to likewise engage the outer cylindrical surface of the mounting pole with a side of the finger generally tangential thereto. These first and second sets of fingers are shorter in length than the arms and are preferably spring like or yieldable to accommodate variations in pole size and maintain a gripping bias against the surface of the support pole. The yieldability or spring characteristics thereof may be provided by the material from which the integral clamp is constructed, as well as thickness of the gripping finger structure. The clamp may be made of any suitable material, such as any of the moldable plastics.

A gripping or engaging pad 46 may also be provided on the inner surface of the latch finger 20. Thus, as can be seen in FIG. 1, the combination of arms and latching fingers extend inward and are latched into a gripping engagement with the outer cylindrical surface of a support pole 12. The illustrated embodiment is designed to accept two sizes of support poles, these being five-eighths of an inch and seven-eighths of an inch. Different sizes may be accommodated by different size clamps or an elongated continuous set of ratchet teeth along the inner surface of the latch finger 22.

Figure 2:
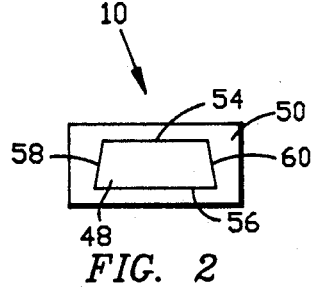
FIG. 2 is a view taken on line 2—2 of FIG. 1.

The clamp 10 is designed to accept and mount a variety of medically related implements to a vertical IV support pole or tube. The clamp is therefore provided with means for attaching various devices or implements to the face of the clamp body 14. In the illustrated embodiment, the clamp is provided with a wedge type mounting bracket, as best seen in FIGS. 1 and 2, generally trapezoid shape panel 48 mounted and spaced outward from a front face 50 of the clamp body 14 by means of a similar shaped smaller trapezoidal member 52. The panel 48, as shown in FIG. 2, has a pair of parallel upper and lower edges 54 and 56, with a pair of sloped side edges 58 and 60.

Figure 4:
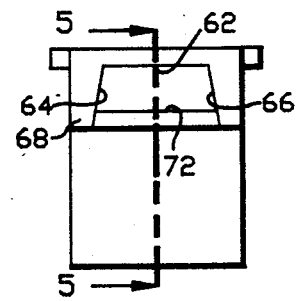
FIG. 4 is view taken on line 4—4 of FIG. 3; a front elevation view in section of the embodiment of FIG. 2.
Figure 5:
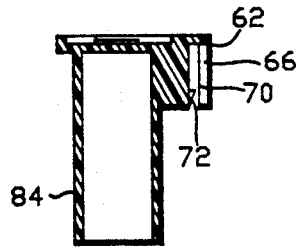
FIG. 5 is a section view taken on line 5—5 of FIG. 4.

The mounting bracket is designed to receive a panel, as shown in FIG. 4, having a similar shaped central opening defined by a wall spaced outward from an inner wall. The opening is formed of an upper edge 62, with sloped side edges 64 and 66 extending downward and through a central area of a lower edge 68 of the spaced panel. As shown in FIG. 5, this outwardly spaced panel forms a slot 70 for receiving the panel 48 of FIG. 2.

A latching edge or barb 72 may be provided at the lower edge of the inner wall of the opening, as shown in FIGS. 4 and 5, for extending under and engaging the lower edge 56, as shown in FIG. 2, for locking the two parts together. With this arrangement, a plurality of identical clamps can be made for permanent attachment to a plurality of articles to be supported. The clamp and respective article may be separately manufactured and secured together in a somewhat permanent attachment for providing a disposable unit.

In the illustrated embodiment, the unit is illustrated and designed to accept a needle sheath or cap holder. The sheath or cap holder comprises a basic body member 76 formed with an outwardly extending somewhat oval surface 76 having an upstanding rim 78, and a pair of sheath or cap receiving holes 80 and 82. The holes 80 and 82 are sized and shaped for receiving conventional injection needle caps or sheaths. Other forms of holes may also be provided. The rim 78 prevents the end of a needle from slipping off the surface 76 if it misses the sheath or cap.

A downwardly depending skirt 84 of a somewhat oval configuration shields and hides the sheaths to prevent a user from instinctively grasping the sheath to steady it as the needle is being reinserted therein. This aids in avoiding the pricking of a hand while re-sheathing the needle. Such needle re-sheathing devices are referred to as passive needle re-sheathing devices.

Figure 6:
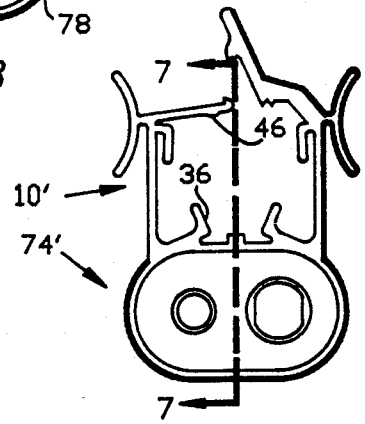
FIG. 6 is a top plan view of an alternate embodiment of the invention.

Referring to FIGS. 6 and a unitary combination clamp and re-sheathing device is illustrated. This illustrates that, for example, the clamps may be made separately for connection to an article to be supported or it may be integral therewith.

Figure 7:
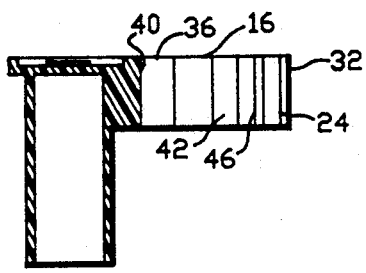
FIG. 7 is a section view taken on line 7—7 of FIG. 6.

Referring to FIGS. 6 and 7, wherein like elements will be identified by the same number and equivalent elements will be identified by the same number prime, the clamp itself, but for the existence of the mounting clip, is identical to the clamp of FIG. 1. The clamp in this embodiment is made integral with a needle sheath or cap holder identical to that illustrated in FIGS. 3-5, but for the detachable connector for connecting to a clamp or the like. Thus, the entire combination of the clamp and the needle sheath or cap holder is formed of an integral unit.

Figure 3:
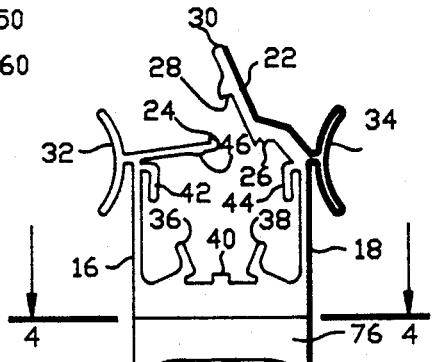
FIG. 3 is a top plan view of the embodiment of FIG. 1 attached to a needle cap holder.

In use, a device to be mounted on a support rod is selected and mounted to a clamp, as shown in FIG. 1. This mounting creates a unit, such as shown in FIG. 3, which may then be mounted to a vertical extending support pole, such as an IV support pole. To attach the device or clamp around the pole, the arms and outer latch fingers are spread apart and extend around the cylindrical support pole. The arms and latch fingers are brought together with a finger and thumb engaging the squeeze tabs 32 and 34, forcing them toward one another. This results in the arms 16 and 18 bending in toward the support pole, with the gripping fingers 32, 38, 42 and 44 engaging the surface of the support pole as the inner and outer fingers 20 and 22 are brought into latching engagement.

The latching can be accomplished by one hand. In a similar manner, the clamp can be released simply by engaging the outer release tab 30, with a finger or thumb and prying it outward. This pulls the ratchet teeth 28 out of engagement with the tooth or hook 24, and releases the clamp so that it may be removed from the support pole.

Figure 8:
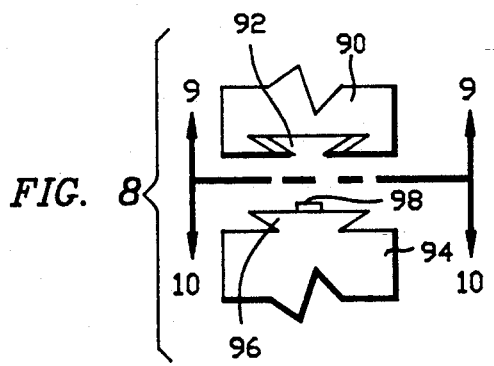
FIG. 8 is an exploded top view of an alternate mounting bracket.
Figure 9:
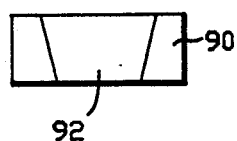
FIG. 9 is a view taken on line 9—9 of FIG. 8.
Figure 10:
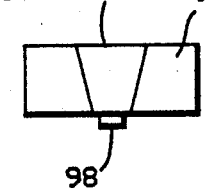
FIG. 10 is a view taken on line 10—10 of FIG. 8.

Referring to FIGS. 8-10, an alternate mounting or attachment bracket is illustrated. In this embodiment, one of the clamp and article 90 is provided with a slightly tapered slot 92. The other of the clamp and article 94 is provided with a similar shaped block or rail 96 that slides and wedges into the slot 92. A latch or lock barb 98 at the bottom of 96, similar to 72 of FIG. 5, locks the two members 90 and 94 together. The slot is preferably formed on the clamp member so it is adapted to receive certain clips formed on the article to be supported.

While we have illustrated and described our invention by means of specific embodiments, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

We claim:

1. A mounting clamp for detachably mounting an article to vertically oriented support poles of different diameter, comprising:
   a base member having gripping means thereon for gripping engagement with a surface of a support pole;
   a pair of spaced apart opposed arms having an inner end and an outer end and attached at said inner end to said base and extending outward from said base substantially parallel to one another forming a pole gripping area therebetween;
   a plurality of yieldable gripping fingers, each having a length less than that of said arms extending outwardly at an angle from opposing surfaces of said arms toward said pole gripping area for tangential gripping engagement with the vertically oriented surface of a support pole on an opposite side of said pole from said gripping means on said base so that a pole is gripped between said fingers and said gripping means;
   adjustable latching means at the outer ends of said arms for cooperative latching engagement and cooperative with said yieldable gripping fingers for selective attachment of said arms around vertical support poles of different diameter; and
   finger squeeze pads on the outer end of said arms for engagement by opposed fingers for forcing said arms together to a selected latched position around a support pole.

2. A mounting clamp according to claim 1 wherein said gripping fingers are curved for engaging a support pole tangentially.

3. A mounting clamp according to claim 1 further comprising a pair of fingers on said base extending toward said pole gripping area.

4. A mounting clamp according to claim 1 wherein said latch means comprises an outer finger on one of said arms overlapping an inner finger on the other of said arms, said fingers having ratchet means for latching engagement, and said outer finger includes a release tab for releasing said engagement.

5. A mounting clamp according to claim 1 wherein said arms extend outward generally parallel when in the unlatched position.

6. A mounting clamp according to claim 1 wherein said base means includes means for attachment to an object to be supported.

7. A mounting clamp for detachably mounting an article to vertically oriented support poles of different diameter, comprising:
   a base member having gripping surface means thereof for gripping engagement with a surface of a support pole;
   a pair of spaced apart opposed arms having an inner end and an outer end and attached at said inner end to said base and extending outward from said base substantially parallel to one another forming a pole gripping area therebetween;
   a plurality of yieldable gripping fingers, each having a length less than that of said arms extending outwardly from opposing surfaces of said arms toward said pole gripping area for gripping engagement with the vertically oriented surface of a support pole wherein said gripping fingers are generally L-shaped with outer ends aligned to engage a surface of a cylindrical member tangentially to the surface thereof;
   adjustable latching means at the outer ends of said arms for cooperative latching engagement and cooperative with said yieldable gripping fingers for selective attachment of said arms around vertical support poles of different diameter; and
   finger squeeze pads on the outer end of said arms for engagement by opposed fingers for forcing said arms together to a selected latched position around a support pole.

8. A mounting clamp for detachably mounting an article to a support pole, comprising:
   a base member having a vertical surface and a wedge slot for receiving a wedge attachment means on an article to be supported;
   a pair of opposed arms having an inner end and an outer end and attached to said base at said inner end;
   a plurality of gripping fingers extending inwardly from the opposing surfaces of said arms for gripping engagement with the surface of a support pole;
   latching means at the outer ends of said arms for cooperative latching engagement; and
   finger squeeze pads on the outer end of said arms for engagement by opposed fingers for forcing said arms together to a latched position around a support pole.

9. A mounting clamp according to claim 8 further comprising a pair of fingers extending outward from said base.

10. A mounting clamp according to claim 9 wherein said clamp has a height of on the order of about one-half of an inch.

11. A mounting clamp for detachably mounting a medical device to multiple sizes of vertical support poles, comprising:
   a base member having an inner face and a generally rectangular outer face said outer face includes a vertical surface and a wedge slot for receiving a wedge attachment means on an article to be supported thereon;
   a pair of opposed arms having an inner end and an outer end and attached to said base at said inner end and extending outward substantially parallel to one another from the inner face of said base;
   an outwardly extending latching finger on the outer end of each of said arms, each of said latching fingers having ratchet means thereon for overlapping mutual latching engagement, and one of said fingers includes a release tab extending outward from an outer end thereof;
   a pair of yieldable gripping fingers extending outwardly at an angle from the opposing surfaces of said arms for tangential gripping engagement with the surface of a substantially cylindrical support pole;
   a pair of yieldable gripping fingers extending outwardly from said base for gripping engagement with the surface of a substantially cylindrical support pole; and
   finger squeeze pads on the outer end of said arms for engagement by a pair of opposing fingers for forcing said arms together to a latched position around a support pole.

12. A mounting clamp for detachably mounting a medical device to multiple sized of vertical support poles, comprising:
   a base member;

a pair of opposed arms having an inner end and an outer end and attached to said base at said inner end and extending outward substantially parallel from said base;

a latching finger on the outer end of each of said arms for mutual latching engagement;

a pair of yieldable gripping fingers extending inwardly from the opposing surfaces of said arms for engagement with the surface of a substantially cylindrical support pole;

a pair of yieldable griping fingers extending inward from said base for gripping engagement with the surface of a substantially cylindrical support pole, said gripping fingers extend at an angle to said arms for engaging a support pole tangentially; and finger squeeze pads on the outer end of said arms for engagement by a pair of opposing fingers for forcing said arms together to a latched position around a support pole.

13. A mounting clamp according to claim 12 wherein said gripping fingers have a generally L configuration.

14. A mounting clamp according to claim 13 wherein one of said latch fingers includes a release tab extending outward from an outer end thereof.

15. A mounting clamp according to claim 12 wherein one of said latch fingers includes a release tab extending outward from an outer end thereof.

16. A mounting clamp according to claim 15 wherein said base means includes means for attachment to an object to be supported.

17. A mounting clamp for detachably mounting a medical device to multiple sizes of vertical support poles, comprising:

a base member having a vertical surface and a wedge slot for receiving a wedge attachment means on an article to be supported;

a pair of opposed arms having an inner end and an outer end and attached to said base at said inner end and extending outward substantially parallel from said base;

a latching finger on the outer end of each of said arms, said fingers having ratchet means for mutual latching engagement, and one of said fingers includes a release tab extending outward from an outer end thereof;

a pair of yieldable gripping fingers extending outwardly at an angle from the opposing surfaces of said arms for tangential engagement with the surface of a substantially cylindrical support pole;

a pair of yieldable gripping fingers extending outward from said base for gripping engagement with the surface of a substantially cylindrical support pole; and finger squeeze pads on the outer end of said arms for engagement by a pair of opposing fingers for forcing said arms together to a latched position around a support pole.

18. A mounting clamp for detachably mounting a medical device to multiple sizes of vertical support poles, comprising:

a base member having an inner face and a generally rectangular outer face;

a pair of opposed arms having an inner end and an outer end and attached to said base at said inner end and extending outward substantially parallel to one another from the inner face of said base;

an outwardly extending latching finger on the outer end of each of said arms, each of said latching fingers having ratchet means thereon for adjustable overlapping mutual latching engagement;

a first pair of yieldable gripping fingers, said fingers having a length less than that of said arms extending outwardly from the opposing surfaces of said arms for gripping engagement with the surface of a substantially cylindrical support pole wherein said gripping fingers extend at angle to said arms for engaging a support pole tangentially;

a second pair of yieldable gripping fingers extending outward from said base for gripping engagement with the surface of a substantially cylindrical support pole; and finger squeeze pads on the outer end of said arms for engagement by a pair of opposing fingers for forcing said arms together to a latched position around a support pole.

19. A mounting clamp according to claim 18 wherein one of said latch fingers includes a release tab extending outward from an outer end thereof.

* * * * *